United States Patent [19]

Lange et al.

[11] Patent Number: 5,116,115
[45] Date of Patent: May 26, 1992

[54] METHOD AND APPARATUS FOR MEASURING CORNEAL TOPOGRAPHY

[75] Inventors: Steven R. Lange; Edmond H. Thall, both of Tucson, Ariz.

[73] Assignee: Wyko Corporation, Tucson, Ariz.

[21] Appl. No.: 521,487

[22] Filed: May 9, 1990

[51] Int. Cl.$^5$ .............................................. A61B 3/10
[52] U.S. Cl. ..................................... 351/212; 351/219
[58] Field of Search ........... 351/212, 219, 160, 160 R, 351/160 H

[56] References Cited

U.S. PATENT DOCUMENTS 4,309,085  1/1982  Morrison ............................ 351/219
4,984,893  1/1991  Lange ................................. 356/376

*Primary Examiner*—Paul M. Dzierzynski
*Attorney, Agent, or Firm*—Cahill, Sutton & Thomas

[57] ABSTRACT

A thin, flexible, reflecting diffuse material is placed or formed on an anterior surface of a cornea. The material has properties that precisely conform to changes in shape of the cornea. This allows remote sensing of the shape of the cornea by projected fringe contouring.

18 Claims, 2 Drawing Sheets

METHOD AND APPARATUS FOR MEASURING CORNEAL TOPOGRAPHY

BACKGROUND OF THE INVENTION

Various ophthalmometers that measure the shape of a patient's cornea have provided physicians with important information for over a century. Such devices measure individual variation in average paracentral corneal radius of curvature. However, ophthalmometers do not actually measure the entire corneal topography. Instead, they assume that the central 3 to 4 millimeters of the cornea is a toroidal surface, and measure its "average" radius of curvature in two perpendicular meridians. This assumption is reasonable for normal corneas. Modern ophthalmometers are calibrated to read corneal radius of curvature in "diopters" rather than in millimeters.

Various methods for using ophthalmometers and other devices have been used to measure the cornea. The majority of these treat the cornea as a close approximation to a convex sphere, and require a specularly reflecting surface. These two requirements often preclude the use of such methods intraoperatively or in pathologic cases.

Ophthalmometers, modern versions of which are called keratometers, are indispensable for fitting rigid contact lenses. Keratometers now also are used to estimate the power of intraocular lens (IOL) implants, i.e., to measure the corneal refractive power and then calculate the IOL power required. Keratometers also are used in operating rooms to make corneal measurements which hopefully help the surgeon minimize postoperative astigmatism in cataract surgery by measuring the average astigmatism of the cornea in the center thereof.

A problem with keratometers is that they do not measure the actual corneal topography, but merely the "average" radius. The central region of the cornea, which is the most important optically, is not evaluated. A specularly reflecting surface (i.e., a surface which reflects in accordance with Snell's law) is required, and the measurements are not very reproducible because the cornea is not precisely spherical, so the result of a measurement depends on where the non-spherical cornea measurement is taken. Various improvements in keratometers have been proposed, but have met with limited success because certain fundamental problems, subsequently discussed, have not been solved.

In normal eyes, the interfaces 3A, 3B, 2A, and 2B of the ocular media, as shown in FIG. 1, specularly reflect a small amount of incident light. Since these are optical surfaces, catoptric images (i.e., virtual images) are formed by each of the four interfaces. The magnification of these images depends on the curvature of the reflecting surface. All of the currently used clinical instruments measure the size of images formed by the anterior corneal surface (called the first Purkinje image) which can be used to calculate the radius of curvature.

Typically, keratometers project a luminous object of known dimension onto the cornea, and the size of the reflected image (called the mire) is measured. Alternatively, the object size is varied until an image of specified size is obtained (as in the Javal-Shiotz keratometer). From this information the image magnification, and in turn the corneal curvature, can be determined.

It also should be appreciated that the size and curvature of the cornea require that the illuminated pattern of concentric circular rings be very large (i.e., twelve inches in diameter if it is located well away from the eye to allow access during surgery), or else if it is small (i.e., one inch in diameter), it must be very close to the eye in order to have a virtual image the size of the cornea. This prevents the surgeon from gaining access to the eye while measurements are being made. If the concentric circular pattern is very large (i.e., twelve inches in diameter), then "shadowing" caused by the nose and eyebrow will prevent data from being accurately measured in the shadowed regions.

A major problem in measuring the mire size is that the living eye, and consequently the reflected image, constantly moves. To deal with this problem, a translatable biprism is placed in the viewing telescope, as shown in FIG. 2, to produce two complete mires. The displacement of the images can be altered by changing the separation between the objective and the biprism. As the eye moves, both images translate in tandem. The observer adjusts the biprism so that the mires are tangent, and the reflected image size can be determined by the biprism position. The corneal curvature then can be calculated from the measured size thereof and various optical layout distances of the measurement instrument.

This technique has several inherent disadvantages. First, it does not measure the corneal topography, but merely the average radius of curvature between two points in each of two perpendicular meridians. This is of little value if, as in most pathologic cases, the central cornea bounded by these pints is not regular (spherical or toroidal).

Thus, the translatable biprism technique fails in precisely those instances in which topographic data would be most valuable. Furthermore, the central cornea, the region most important visually, is not measured at all. The lack of topographic data for the central cornea limits the applicability of translatable biprism devices in even routine situations (e.g. contact lens fitting for regular corneas).

A second disadvantage of keratometers is that there is no way to reproducibly align the instrument. Even normal corneas are somewhat aspheric, so each area of the cornea has a different radius of curvature. Thus, measurements cannot be repeated. The translatable biprism keratometer contains a fixation system that limits measurements to the same general vicinity. However the inability to repeatably measure the same spot makes it difficult to follow progressive contour changes, which is valuable in certain diseases. Further, the fixation system cannot be used by patients with poor acuity, which s common in corneal disease. In nonfixating patients (i.e., those who cannot see well enough to fixate on an illuminated target), the machine can be only grossly aligned, severely limiting the keratometer's utility for monitoring progression of corneal disease.

A third disadvantage of translatable biprism keratometers is that they require that the reflected image lie in a plane. If the two test points (on a given meridian of the cornea) are associated with significantly different curvature, they cannot be simultaneously imaged, and a measurement cannot be made. This is frequently the case when the cornea is irregular. Consequently, the translatable biprism keratometer cannot measure rotationally asymmetric corneas, which is problematic because diseased corneas frequently are rotationally asymmetric.

Fourth, the cornea must be specularly reflecting. Epithelial edema, opacities, surface asperities, etc. preclude the use of translatable biprism keratometer techniques. This is especially problematical in an operating room, where even normal corneas frequently are temporarily rendered diffusely reflective by surgical manipulation, i.e., by abrading epithelial cells from the cornea.

The most serious of the foregoing problems is that keratometry does not provide topographic data for the center of the cornea. Nonsphericity in the cornea is indicated by deviations from circularity in the image. For instance, a toric cornea produces elliptically shaped rings, the long axis indicating the largest radius of curvature. Several efforts to overcome this have been devised.

Keratoscopes use targets composed of multiple coaxial circles, usually in a three dimensional arrangement (e.g. cylindrical, spherical, or conical). In order to cover the entire cornea, the target must subtend a large angle at the eye and should not be shadowed by facial features such as the nose, eyelid, or eyebrow. The mathematical analysis of the reflected image depends on the target geometry, and can be significantly simplified by a judicious choice of target architecture. The keratoscope may be fitted with a photographic or video camera, in which case it is called a photokeratoscope. Photographs can be measured and analyzed quantitatively, or video cameras can be directly interfaced to computers which analyze the data received.

To overcome the alignment problems, several autocollimating techniques have been advocated. These systems use the anterior corneal vertex as a reference point for aligning the instrument. In the short term, this improves the measurement reproducibility. However, the greatest need for repeatable measurements is under conditions in which the corneal topography changes over time. In these cases, the vertex position also changes significantly. Since the vertex position used for alignment is not constant, this method is of limited value in such cases. Autocollimating keratoscopes improve the accuracy of keratoscopy for applications such as contact lens fitting. However, they are expensive and difficult to use, and do not improve contact lens fitting sufficiently to overcome their negative qualities. None has been commercially successful.

Neither keratometry (which projects a single ring) nor keratoscopy (which projects many rings) can measure highly irregular corneas because the first Purkinje image cannot be observed for irregular corneas. The image produced by a highly irregular cornea does not lie in a single plane, as shown in FIG. 3. If the axial extent of the image exceeds the depth of focus of the optics used to observe the image, some data will be lost. The problem is often severe enough to prevent a meaningful measurement. Even regular corneas with radii of curvature beyond the limits of the observation optics cannot be measured.

Both keratoscopy and keratometry rely on images formed by specularly reflecting surfaces. Even if the cornea topography is regular, certain medical conditions, such as opacities, inflammation, epithelial edema, abrasions, etc., may render it nonspecular. Keratoscopy and keratometry techniques fail in such cases.

Stereophotogrammetric techniques have been employed to overcome this problem. In this approach, a three dimensional reconstruction of the cornea is made from two preferably simultaneous photographs taken at different angles. To accomplish the three dimensional reconstruction, there must be a number of readily identifiable "landmarks" on the corneal surface. Talcum powder has been used experimentally to provide such "landmarks". A pattern projected on a fluorescein covered cornea also has been proposed as such a fiducial marking. This approach requires the fiducial pattern be on the corneal surface. Fluorescein, however, diffuses throughout the cornea and into the anterior chamber of the eye, making a surface measurement impossible. A soft, flexible contact lens with 200 fiducial marks on its posterior surface has been used with limited success. Stereophotogrammetric techniques cannot be used in the operating room because the fluorescein cannot be localized to the anterior corneal surface, and talcum powder cannot be used in an open surgical procedure in an operating room.

SUMMARY OF THE INVENTION

Accordingly, it is an object of the invention to provide a technique for measuring the height distribution of the anterior surface of the cornea of the eye.

It is another object of the invention to provide a technique for determining the height distribution of the anterior surface of the cornea in the presence of medical conditions that would render the surface of the cornea non-specularly reflecting.

It is another object of the invention to provide an apparatus for determining the height distribution of a cornea in the presence of a corneal surface which is badly distorted, either naturally or by surgery.

It is another object of the invention to provide a device for producing a map of the surface heights over the central region of the cornea.

It is another object of the invention to allow the measurement of the cornea without mechanical structures close to the eye.

It is another object of the invention to provide a device which allows a surgeon to make measurements of the anterior surface of a cornea during a surgical procedure.

It is another object of the invention to provide a device able to give a surgeon feedback on the shape of the cornea during a surgical procedure so that the surgeon can correct or alter the shape.

It is another object of the invention to measure an area of the cornea out to the limbus and/or the region where sutures are inserted.

It is another object of the invention to measure a cornea without having to align an instrument to be centered on the optical axis of the eye.

It is another object of the invention to measure an entire corneal surface without being subject to shadowing caused by the nose, eyelashes, or eyelid.

It is another object of the invention to provide a device and method for measuring the entire surface of a cornea even in the presence of local irregularities or local regions that are not specularly reflecting.

Briefly described and in accordance with one embodiment thereof, the invention consists of a method and apparatus for profiling the anterior surface of the cornea, placing a thin, elastic, diffusely reflecting cover material on the cornea so that the cover material conforms to the shape of the cornea, projecting a structured light pattern such as a sinusoidal grating pattern on the corneal cover and shifting the phase of the structured light pattern, operating a detector to view the structured light pattern on the corneal cover, digitizing intensities of signals from the detector, transferring the digitized intensities to a computer, computing a phase of each point on the cover material, and calculating the height distribution over the cover material from the computed phase for each point, respectively. The topography of the cornea is then displayed from the relative heights thereby obtained. In the described embodiment, the detector is a video camera, and the structured light pattern is a sinusoidal grating pattern projected by a phase-shifting slide projector onto the corneal cover from a distance of at least approximately five to six inches, or at least enough to allow presence of a surgeon's hands. A physician can view the cornea and cover material through a surgical microscope and monitor the topography of the cornea as a surgical procedure is performed.

DETAILED DESCRIPTION OF THE PREFERRED EMBODIMENT

Figure 4:
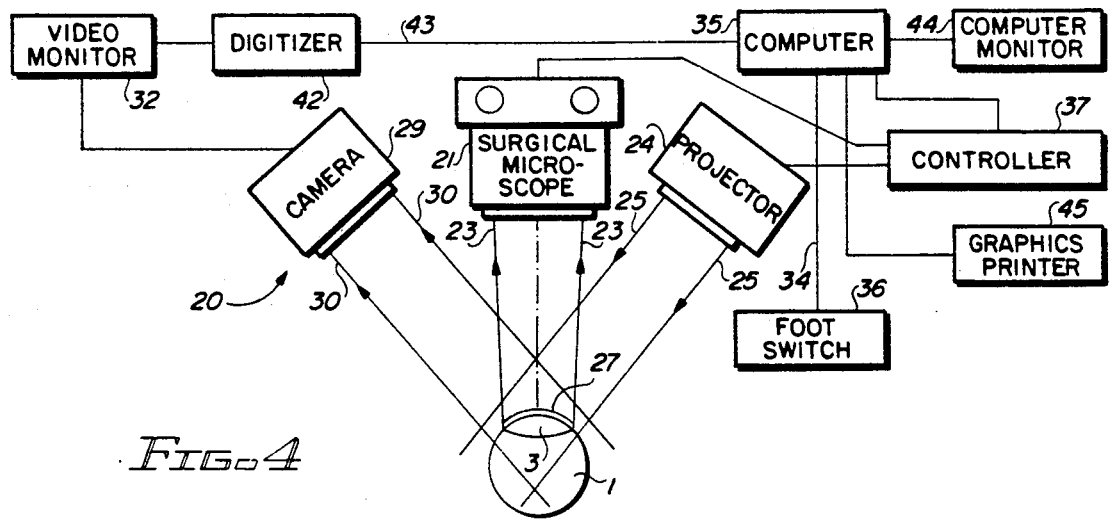
FIG. 4 is a block diagram of the corneal measurement system of the present invention.

Referring to FIG. 4, corneal topography measurement device 20 includes a projected fringe contouring system attached to a surgical microscope 21. The surgical microscope both illuminates cornea 3 of eye 1 and allows the surgeon to view cornea 3 under a variable magnification as indicated by rays 23. A phase-shifting slide projector 24 illuminates the cornea of eye 3 with a linear sinusoidal intensity pattern or grating, as indicated by rays 25. Slide projector 24 can be implemented in a variety of ways by those skilled in the art, and preferably by the device described in commonly assigned pending patent application entitled "PHASE SHIFTING DEVICE AND METHOD" filed on Dec. 1, 1989, Ser. No. 444,542, by Steven R. Lange, now U.S. Pat. No. 4,984,893, issued Jan. 15, 1991, incorporated herein by reference. (Alternatively, a laser interferometer having phase-shifting capability could be used.) As indicated in FIG. 5A, the direction of the grating or pattern should be perpendicular to the direction of illumination. For the present invention, the dark lines of grid pattern 4 can be approximately 8 to 10 millimeters wide, and can be about one-half of a millimeter apart.

Figure 1:
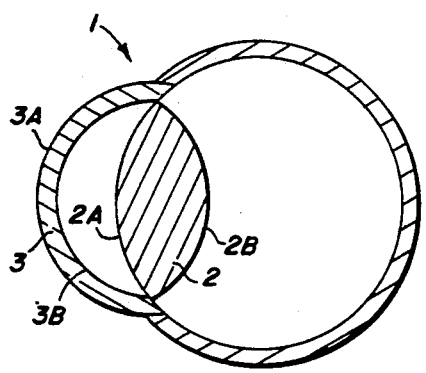
FIG. 1 is a schematic diagram of a human eye showing four interfaces of the ocular media which produce the four Purkinje images.
Figure 3:
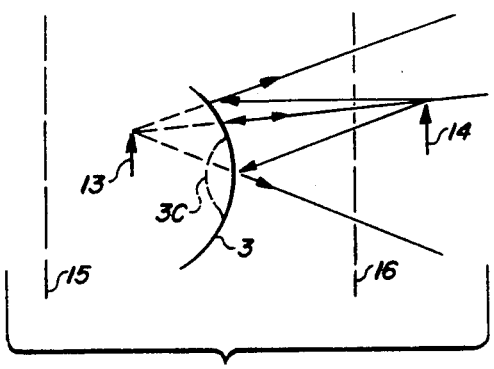
FIG. 3 is an illustration showing that the first Purkinje image does not lie in a plane when the cornea topography is irregular.
Figure 2:
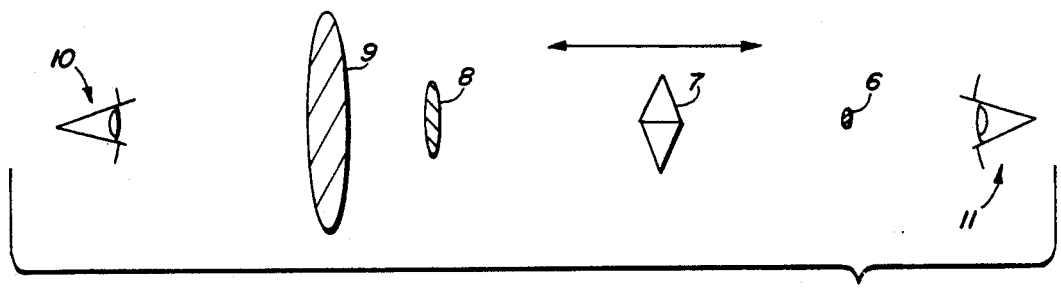
FIG. 2 is a schematic diagram of a manual keratometer illustrating the use of the doubling principle.
Figure 5B:
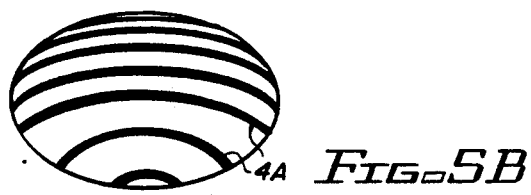
FIG. 5B is an illustration showing a camera's view of the projected grating with the camera oriented at an angle to the projected image of FIG. 5A.
Figure 5A:
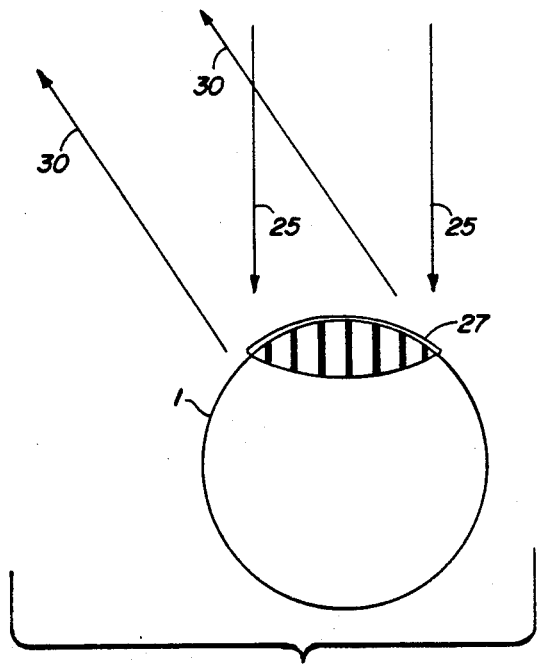
FIG. 5A is an illustration showing projected grating on a cornea.
Figure 5C:
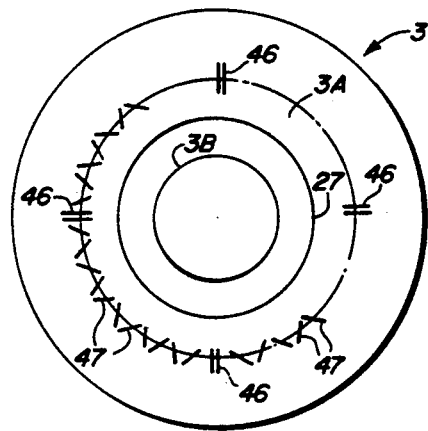
FIG. 5C is a plan view illustrating the corneal cover of the present invention in place on a transplanted "corneal plug".

Referring to FIGS. 5A-5C, a white or highly diffusely reflecting thin film 27 of material is draped over the cornea of eye 1 and conforms precisely to the shape of the anterior surface of cornea 3. The properties of the material 27 are such that a beam of light striking it will be diffusely reflected. That is, the incident beam of light will not be preferentially reflected at an angle equal to the incident angle according to Snell's law. Film 27 should be uniformly thin so as to not alter the height distribution calculated for the cornea 4 which it maps. Film 27 should be fabricated from material that can be easily sterilized and is non-toxic to the human body or the open eye. Film 27 also must have the property of being flexible and somewhat elastic in order to conform precisely to the curvature of cornea 3 even when the cornea is distorted, yet must not be so friable or flexible as to cause the surgeon undue difficulty in handling it. Thin, white TEFLON tape (for example, ordinary plumber's tape), cut into small circles having the same diameter as the cornea 4 or a part of the cornea desired to be measured, is a material having the needed properties. This kind of TEFLON tape is approximately 0.004 inches thick. It is white, somewhat elastic, and conforms quite well to the shape of a cornea 3 on which it is placed.

It should be appreciated that the earlier described prior instruments for contouring the cornea all are based on the assumptions that the surface of the eye acts as a convex reflective mirror forming a virtual image of a pattern and that parameters associated with the size and shape of the virtual image can be measured to determine the shape of the cornea. If the surface of cornea 3 is not smooth on a cellular level, the cornea may not act like a mirror. The result is that no virtual image is formed or only a poor image is formed, so there is no suitable image to measure with a camera or detector. If this condition occurs, either locally within the camera or globally over the entire cornea, no data can be obtained from those regions where the cornea is not mirror-like using prior keratometers or keratoscopes. The use of TEFLON film 27 has been found to eliminate most difficulties that have been encountered with such prior corneal measurement instruments of the kind that "assume" the eye is a specular, optical surface.

In FIG. 4, a conventional video camera 29 is positioned to view the projected sinusoidal intensity or grating pattern 4 on cornea 3 of eye 1 by receiving rays 30 at a different angle than rays 25 from projector 24. Camera 29 sees grating pattern 4 not as a set of parallel lines as they are projected, but as a distorted, non-parallel, unequally spaced, curved set of lines 4A illustrated in FIG. 5B. The height of each point of the cornea relative to a hypothetical reference plane is represented by the degree of non-parallelism and the spacing changes of the camera-observed pattern 4A.

The phase shifting slide projector 24 and camera 29 can be located at a large enough distance from the eye (i.e., at least approximately five to six inches) to provide ample space for the surgeon to make necessary manipulations of the eye and use various surgical instruments without having to remove or relocate the slide projector or camera. Camera 29 and slide projector 23 can be easily positioned or changed in magnification so that the entire cornea 3 can be illuminated by slide projector 24 and seen by camera 29 and thus be measured without interference by shadowing from the nose or eyebrow if the cornea remains within the depth of focus of both the camera lens and projector lens.

In FIG. 4, a video monitor 32 is coupled to camera 29 and shows live video coming from camera 29 to monitor the alignment of the video camera and the projector. The cornea must be centered in the field of view of the video camera and the projected fringe pattern from the projector must fully illuminate the cornea. The surgical lamp is turned off when the projector lamp is turned on to minimize the unwanted light during a measurement, although suitable filtering of the projector and camera could avoid the need for this.

FIG. 5C shows a plan view of a corneal transplant plug 3A, which is usually 7 to 8 millimeters in diameter, in cornea 3. The diameter of cornea 3 at the limbus is about 12 millimeters. The placement of cornea cover 27, which may be approximately 6 to 7 millimeters is diameter, is shown. Numeral 3B shows the 3 to 4 millimeter diameter "active visual area" of the cornea. The cornea transplant 3A is initially sutured at its four "cardinal points" to original cornea 3 by four "cardinal sutures" 46. The periphery of corneal plug 3A is sutured by running sutures 47 to the original cornea 3.

During a surgical procedure, a condition may occur wherein the surgeon desires to know the topography of the cornea in order to know how much to tighten the sutures 46 and 47. He can initiate measurement and generation of data by a signal 34 to a computer 35 by either a foot activated switch 36 sensed by computer 35 or by a keyboard command. (Computer 35 can be a Model PC-AT available from IBM, operating with software named WISP, available from the Assignee.) When such an initial signal 34 is received by computer 35, a computer program directs the lamp of slide projector 24 to be turned on through a signal 36 to a controller 37. Controller 37 produces signals on conductors 39 and 40 to turn on the lamps of surgical microscope 21 and turn off slide projector 24. Controller 37 also controls phase shifting of beam 25 by slide projector 24 by other signals on conductor 40.

A frame grabbing digitizing board 42 associated with computer 35 then digitizes frames of data coming from camera 29 and sends them via signals 43 to computer 35. (Frame grabbing digitizer board can be a Publisher's VGA available from Willow Peripherals, Inc. of N.Y.) Any of a number of known techniques can be used to determine the height distribution over the anterior surface of cornea 3 from the structured light grating or sinusoidal pattern 4 being projected on cornea 3.

Figure 6A:
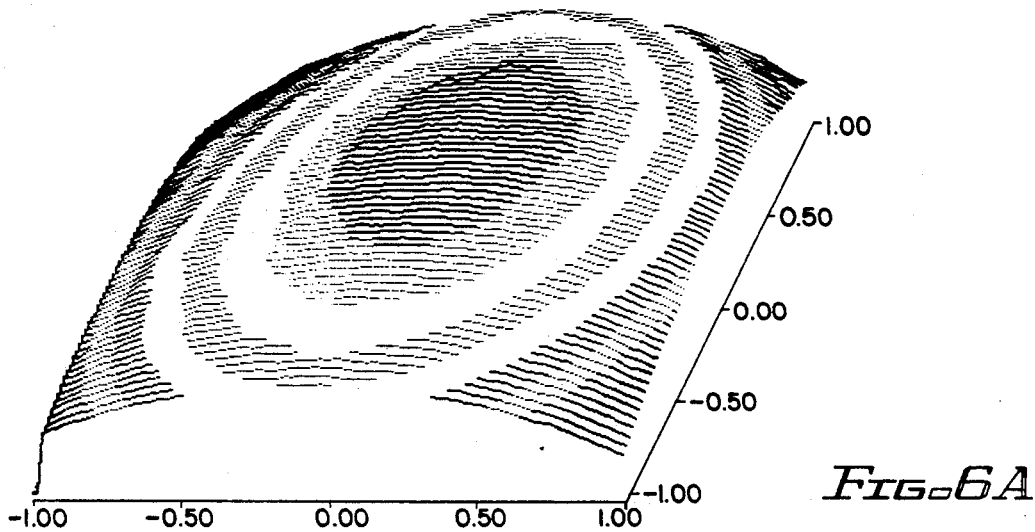
FIG. 6A is a diagram of a plot of a measured normal spherical cornea in accordance with the invention.

The present embodiment of the invention generates a display such as that shown in FIG. 6A,B in approximately 25 seconds, although it is believed that this could be reduced to approximately 5 seconds by using a faster computer based on an 86386 microprocessor chip and simplifying the above WISP software algorithm.

The technique used in the presently preferred embodiment uses a well known phase-shifting interferometry technique which calculates the phase of the sinusoidal pattern observed at each pixel element or sample point of the intensity pattern observed by camera 29. The computed phase is proportional to the relative height at each sample point, and the constant of proportionality can be calibrated by making a measurement on a reference surface of known height or shape (that is, a calculated amount of phase change can be related to a known step height), and this calibration constant can be used to convert the calculated phases to surface heights. A minimum of three intensity measurements is required to determine the phase since there are three unknowns in the interference equation $$I = I_0(1 + A \cos \phi), \quad (1)$$

where $I_0$ is the average intensity, A is the modulation intensity and $\phi$ is the phase at each detector point.

If the phase is altered by 90 degrees between successive captured video intensity measurements by means of a phase shifting device located in slide projector 24 (for example, the one described in the above-referenced Lange application), then three equations are obtained describing the intensity at each sample point:

$$I_1 = I_0[1 + A\{\cos(\phi - \pi/4)\}] \quad (2)$$

$$I_2 = I_0[1 + A\{\cos(\phi + \pi/4)\}] \quad (3)$$

$$I_3 = I_0[1 + A\{\cos(\phi + 3\pi/4)\}] \quad (4)$$

Solving for the phase $\phi$ results in $$\phi = \arctan[(I_3 - I_2)/(I_1 - I_2)] \quad (5)$$

Equation (1) is applied to each sample point in each of the captured frame video images digitized by the frame grabber circuit 42. The calculation time is very fast because only subtractions and divisions are required. The arctangent can be computed with a lookup table. Note (as is well known) that the arctangent is defined only over 180 ($\pi$) degrees (−90 to +90 degrees and repeats itself thereafter. The arctangent computation results need to be integrated together to establish a continuous surface by adding or subtracting $\pi$ to the calculated points to bring them into line with adjacent sample points.)

Once the frames of intensity data have been captured and digitized and the relative height of all points of cornea 3 have been calculated from the phase data using the phase-to-height proportionality constant, the output can be displayed on computer monitor 44 and also printed by means of a graphics printer 45. The display or printout can take various forms to give information to the surgeon.

In most cases, the surgeon may be interested in the irregularity, or how non-spherical the cornea is. Changes in the average radius of curvature of cornea 3 and irregularities can be corrected surgically by altering the tightness of cardinal sutures 46 and running the sutures 47 of FIG. 5C attaching the transplant plug 3A to the remaining part of the original cornea 3. Irregularities other than pure astigmatism cannot be corrected with either glasses or contact lenses and must be minimized during surgical procedures. The degree of ocular correction of a patient may require after surgery also can be minimized by the surgeon manipulating the shape of the transplanted cornea plug 3A to be as close as possible to a spherical surface of the radius of curvature required for optimum vision.

Figure 6B:
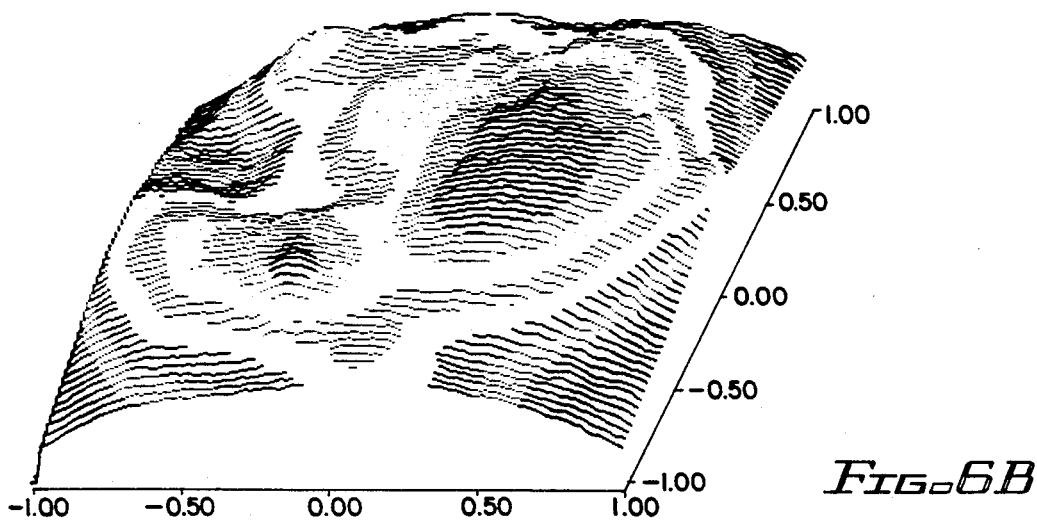
FIG. 6B is a diagram of a plot of a measured irregular cornea in accordance with the invention.

FIG. 6A shows a plot of the results of a measurement of a normal cornea produced by the system of FIG. 4 using a TEFLON tape cornea cover 27 therein. This figure shows the appearance of a normal cornea. FIG. 6B shows a plot of the topography of a TEFLON cornea cover on a cornea during a cornea transplant of a donor eye. The results indicate a very irregular surface requiring a good deal of surgical correction, and illustrate how this technique can be used to measure a surface that is not very spherical.

While the invention has been described with reference to several particular embodiments thereof, those skilled in the art will be able to make the various modifications to the described embodiments of the invention without departing from the true spirit and scope of the invention. Other techniques can be used to determine the height distribution of cornea 3 when cornea cover 27 of the present invention is utilized. For example, the corneal cover would be perforated or in the form of a mesh. The corneal cover could be provided in sections which are separate, or as a plurality of peripheral sections all connected to a center or hub section. The corneal cover could be a diffusely reflecting liquid film. Profiling techniques other than the phase shifting technique described in the presently preferred embodiment could be used. Techniques that sense the distortions of a known projected structured light pattern that do not use phase shifting as described can be employed. For example, known techniques could be used in which the surface profile of the cover 27 is developed from identification of the center of either light or dark bands of the projected pattern. Alternately, known techniques could be used which measure the intensity of each point and compute the profile therefrom. Many algorithms using phase-shifting interferometry other than those described in equations (1) to (5) work equally well. Also, photogrammetry principles using two cameras viewing a featured surface can be employed. Here, the parallax of the two camera views can be correlated on features of the imprinted pattern on the corneal cover to develop a surface height distribution map. Fluorescein liquid could be administered to the cornea to form a thin conforming liquid cover that fluoresces in response to illumination by blue light. This, in effect, renders the cornea surface diffuse, allowing the above-described optical techniques to be used.

What is claimed is:

1. A method for profiling an anterior surface of a cornea, comprising the steps of:
   (a) placing a thin, elastic, diffusely reflecting cover material on the cornea, the cover material conforming to the shape of the cornea;
   (b) operating a slide projector to project a structured light pattern on the cover material and modulating the phase of the structured light pattern;
   (c) operating a detector to view the structured light pattern on the cover material;
   (d) digitizing intensities of signals from the detector, transferring the digitized intensities to a computer, and operating the computer to compute a phase of each point on the cover material;
   (e) operating the computer to calculate the relative height of the cover material from the computed phase for each point.

2. The method of claim 1 wherein step (b) includes operating the slide projector to project a parallel grating pattern on the cover material and repetitively shifting the phase of the grating pattern projected on the cover material.

3. The method of claim 2 wherein step (d) includes digitizing intensities of signals from the detector for each phase, respectively, and operating the computer to compute the phase of each point from intensities of at least three phases of the grating pattern at that point.

4. The method of claim 1 including displaying the topography of the cornea from the relative heights computed in step (e).

5. The method of claim 4 wherein the detector includes a video camera, the method including focusing the video camera and the slide projector onto the cover material from a distance of at least approximately five inches each from the cover material.

6. The method of claim 5 including viewing the cover material through a surgical microscope.

7. The method of claim 6 including performing a surgical operation on the cornea essentially simultaneously with viewing the cornea through the microscope and viewing the topography being displayed.

8. A method for profiling an anterior surface of a cornea, comprising the steps of:
   (a) placing a thin, elastic, diffusely reflecting cover material on the cornea, the cover material conforming to the shape of the cornea;
   (b) projecting a structured light pattern on the cover material and modulating the phase of the structured light pattern;
   (c) operating a detector to view the structured light pattern on the cover material;
   (d) digitizing intensities of signals from the detector, transferring the digitized intensities to a computer, and operating the computer to compute a phase of each point on the cover material;
   (e) operating the computer to calculate the relative height of the cover material from the computed phase for each point.

9. An apparatus for profiling an anterior surface of a cornea, comprising in combination:
   (a) a thin, elastic, diffusely reflecting cover material disposed on the cornea, the cover material conforming to the shape of the cornea;
   (b) means for projecting a structured light pattern on the cover material and modulating the phase of the structured light pattern;
   (c) a detector viewing the structured light pattern on the cover material;
   (d) a computer;
   (e) means for digitizing intensities of signals from the detector and transferring the digitized intensities to the computer;
   (f) means in the computer for computing phases of each point on the cover material for a plurality of phases of the structured light patterns, respectively;
   (g) means in the computer for calculating the relative height of the cover material from the computed phase for each point.

10. The apparatus of claim 9 wherein the cover material is composed of diffusely reflective, plastic film.

11. The apparatus of claim 10 wherein the white, plastic film is TEFLON tape.

12. The apparatus of claim 9 wherein the detector includes a video camera, and the projecting means includes a phase-shifting slide projector.

13. The apparatus of claim 12 wherein the video camera and the phase-shifting slide projector are located at least approximately five inches from the cornea.

14. The apparatus of claim 9 including means for displaying the topography of the cornea in response to the relative height calculated in the computer.

15. The apparatus of claim 13 including a surgical microscope focused on the cover material.

16. The apparatus of claim 15 including means responsive to the computer for actuating an illumination means in the surgical microscope and actuating the slide projector.

17. A method for profiling a surface of a body part that is partially transparent and specularly reflective, the method comprising the steps of:
   (a) placing a thin conformable diffusely reflecting cover material film on the surface, and causing the film to conform precisely to the shape of the body part;

(b) optically measuring the height of a plurality of points of an outer surface of the film by means of a non-contact optical profiler to thereby obtain a surface profile of the surface of the body part.

18. The method of claim 17 wherein step (a) includes administering a drop of diffusely reflecting liquid to the cornea to cause diffuse reflection, the liquid forming the film, and step (b) includes operating the non-contact optical profiler to illuminate the film with light that is reflected from the diffusely reflecting liquid.

* * * * *